(12) United States Patent
Lange

(10) Patent No.: US 11,160,461 B2
(45) Date of Patent: Nov. 2, 2021

(54) BLOOD PRESSURE MEASUREMENT USING A WEARABLE DEVICE

(71) Applicant: ChroniSense Medical Ltd., Yokneam (IL)

(72) Inventor: Daniel H. Lange, Kfar Vradim (IL)

(73) Assignee: ChroniSense Medical Ltd., Yokneam (IL)

( * ) Notice: Subject to any disclaimer, the term of this patent is extended or adjusted under 35 U.S.C. 154(b) by 0 days.

(21) Appl. No.: 15/226,881

(22) Filed: Aug. 2, 2016

(65) Prior Publication Data

US 2016/0360974 A1 Dec. 15, 2016

Related U.S. Application Data

(63) Continuation-in-part of application No. 14/738,666, filed on Jun. 12, 2015, and a continuation-in-part of
(Continued)

(51) Int. Cl.
*A61B 5/0205* (2006.01)
*A61B 5/107* (2006.01)
(Continued)

(52) U.S. Cl.
CPC ............ *A61B 5/0205* (2013.01); *A61B 5/002* (2013.01); *A61B 5/0006* (2013.01);
(Continued)

(58) Field of Classification Search
CPC ..... A61B 5/0205; A61B 5/0006; A61B 5/002; A61B 5/0022; A61B 5/0452;
(Continued)

(56) References Cited

U.S. PATENT DOCUMENTS 3,885,552 A 5/1975 Kennedy
3,898,984 A * 8/1975 Mandel ............... A61B 5/0006
128/903

(Continued)

FOREIGN PATENT DOCUMENTS

CN 1335756 A 2/2002
CN 106901747 A 6/2017
(Continued)

OTHER PUBLICATIONS

Non-Final Office Action, dated Oct. 5, 2016, U.S. Appl. No. 14/738,636, filed Jun. 12, 2015.
(Continued)

*Primary Examiner* — Lynsey C Eiseman
*Assistant Examiner* — Jessandra F Hough
(74) *Attorney, Agent, or Firm* — Carr & Ferrell LLP

(57) ABSTRACT

Systems and methods for performing a blood pressure measurement are provided. An example method includes simultaneously recording, by a wearable device, an electrocardiogram (ECG) and photoplethysmogram (PPG). PPG is measured at a blood artery. The method also includes analyzing ECG and PPG to determine a pulse transit time (PTT), a pulse rate (PR), and a diameter parameter. The diameter parameter includes a diameter of the blood artery or a change thereof. The method also includes determining, based on PTT, PR, and the diameter parameter, a blood pressure (BP) using a pre-defined model. The pre-defined model establishes a relationship between PTT, PR, the diameter parameter, and BP. The pre-defined model may be trained using statistical data obtained in a calibration process. The statistical data includes PTT, PR, and the diameter parameter measured with the wearable device and corresponding values of BP measured with an external device.

20 Claims, 7 Drawing Sheets

Related U.S. Application Data application No. 14/738,636, filed on Jun. 12, 2015, and a continuation-in-part of application No. 14/738,711, filed on Jun. 12, 2015, now Pat. No. 10,470,692.

(51) Int. Cl.
*A61B 5/00* (2006.01)
*A61B 5/1455* (2006.01)
*A61B 5/145* (2006.01)
*A61B 5/349* (2021.01)
*A61B 5/021* (2006.01)
*A61B 5/024* (2006.01)

(52) U.S. Cl.
CPC .......... *A61B 5/0022* (2013.01); *A61B 5/1072* (2013.01); *A61B 5/14546* (2013.01); *A61B 5/14552* (2013.01); *A61B 5/349* (2021.01); *A61B 5/6824* (2013.01); *A61B 5/02125* (2013.01); *A61B 5/02427* (2013.01); *A61B 5/7235* (2013.01)

(58) Field of Classification Search
CPC .............. A61B 5/1072; A61B 5/14546; A61B 5/14552; A61B 5/6824; A61B 5/02125; A61B 5/02427; A61B 5/7235
See application file for complete search history.

(56) References Cited

U.S. PATENT DOCUMENTS

| | | | |
|---|---|---|---|
| 4,331,154 A | 5/1982 | Broadwater et al. | |
| 4,732,158 A | 3/1988 | Sadeh | |
| 4,802,486 A | 2/1989 | Goodman et al. | |
| 5,316,008 A | 5/1994 | Suga et al. | |
| 5,503,148 A | 4/1996 | Pologe et al. | |
| 5,692,505 A | 12/1997 | Fouts | |
| 6,047,203 A | 4/2000 | Sackner et al. | |
| 6,139,494 A | 10/2000 | Cairnes | |
| 6,527,725 B1 | 3/2003 | Inukai et al. | |
| 7,184,809 B1 | 2/2007 | Sterling et al. | |
| 7,479,111 B2 | 1/2009 | Zhang et al. | |
| 7,544,168 B2 | 6/2009 | Nitzan | |
| 7,738,935 B1 | 6/2010 | Turcott | |
| 8,172,764 B2 | 5/2012 | Gregson et al. | |
| 8,602,997 B2 | 12/2013 | Banet et al. | |
| 8,866,606 B1 | 10/2014 | Will et al. | |
| 10,470,692 B2 | 11/2019 | Lange et al. | |
| 10,687,742 B2 | 6/2020 | Lange et al. | |
| 10,952,638 B2 | 3/2021 | Lange | |
| 11,000,235 B2 | 5/2021 | Lange | |
| 2001/0005773 A1 | 6/2001 | Larsen et al. | |
| 2001/0029326 A1 | 10/2001 | Diab et al. | |
| 2002/0095077 A1 | 7/2002 | Swedlow et al. | |
| 2002/0133068 A1 | 9/2002 | Huiku | |
| 2003/0009091 A1 | 1/2003 | Edgar, Jr. et al. | |
| 2003/0036685 A1* | 2/2003 | Goodman | A61B 5/0002 |
| | | | 600/300 |
| 2003/0065269 A1 | 4/2003 | Vetter et al. | |
| 2003/0109776 A1 | 6/2003 | Jacques | |
| 2003/0163033 A1 | 8/2003 | Dekker | |
| 2004/0215095 A1 | 10/2004 | Lee et al. | |
| 2005/0070775 A1 | 3/2005 | Chin et al. | |
| 2005/0215913 A1 | 9/2005 | Lee et al. | |
| 2005/0281439 A1 | 12/2005 | Lange | |
| 2006/0074322 A1* | 4/2006 | Nitzan | A61B 5/021 |
| | | | 600/485 |
| 2006/0264767 A1 | 11/2006 | Shennib | |
| 2007/0142720 A1 | 6/2007 | Ridder et al. | |
| 2007/0191725 A1 | 8/2007 | Nelson | |
| 2008/0146954 A1 | 6/2008 | Bojovic et al. | |
| 2008/0208069 A1 | 8/2008 | John et al. | |
| 2008/0214961 A1* | 9/2008 | Matsumoto | A61B 5/02007 |
| | | | 600/587 |
| 2008/0221419 A1 | 9/2008 | Furman | |
| 2008/0255433 A1* | 10/2008 | Prough | A61B 5/0095 |
| | | | 600/301 |
| 2009/0024011 A1* | 1/2009 | Huiku | A61B 5/14551 |
| | | | 600/323 |
| 2009/0163821 A1 | 6/2009 | Sola I Caros et al. | |
| 2009/0247848 A1 | 10/2009 | Baker, Jr. | |
| 2010/0016694 A1 | 1/2010 | Martin et al. | |
| 2010/0179438 A1 | 7/2010 | Heneghan et al. | |
| 2010/0192952 A1* | 8/2010 | Melker | A61M 16/0627 |
| | | | 128/204.23 |
| 2010/0217144 A1 | 8/2010 | Brian | |
| 2010/0298656 A1* | 11/2010 | McCombie | A61B 5/02028 |
| | | | 600/301 |
| 2010/0312079 A1 | 12/2010 | Larsen et al. | |
| 2010/0324384 A1 | 12/2010 | Moon et al. | |
| 2011/0060200 A1 | 3/2011 | Bernreuter | |
| 2011/0066051 A1 | 3/2011 | Moon et al. | |
| 2011/0077486 A1 | 3/2011 | Watson et al. | |
| 2011/0082355 A1 | 4/2011 | Eisen et al. | |
| 2011/0201946 A1 | 8/2011 | Turcott | |
| 2011/0224564 A1 | 9/2011 | Moon et al. | |
| 2011/0257551 A1 | 10/2011 | Banet et al. | |
| 2012/0190944 A1 | 7/2012 | Thaveeprungsriporn et al. | |
| 2012/0238834 A1 | 9/2012 | Hornick | |
| 2013/0231947 A1 | 9/2013 | Shusterman | |
| 2013/0296665 A1* | 11/2013 | Kassim | G01N 21/3151 |
| | | | 600/310 |
| 2013/0296666 A1 | 11/2013 | Kumar et al. | |
| 2013/0296673 A1 | 11/2013 | Thaveeprungsriporn et al. | |
| 2013/0310700 A1 | 11/2013 | Wiard et al. | |
| 2013/0338460 A1 | 12/2013 | He et al. | |
| 2014/0043164 A1 | 2/2014 | Eschelman et al. | |
| 2014/0088449 A1 | 3/2014 | Nearing et al. | |
| 2014/0142445 A1 | 5/2014 | Banet et al. | |
| 2014/0155705 A1 | 6/2014 | Papadopoulos et al. | |
| 2014/0206948 A1 | 7/2014 | Romem | |
| 2014/0257122 A1 | 9/2014 | Ong et al. | |
| 2014/0275888 A1 | 9/2014 | Wegerich et al. | |
| 2014/0278229 A1 | 9/2014 | Hong et al. | |
| 2015/0109125 A1 | 4/2015 | Kaib et al. | |
| 2015/0148622 A1 | 5/2015 | Moyer et al. | |
| 2015/0157220 A1 | 6/2015 | Fish et al. | |
| 2015/0157262 A1 | 7/2015 | Schuessler | |
| 2015/0196257 A1* | 7/2015 | Yousefi | A61B 5/024 |
| | | | 600/324 |
| 2015/0272510 A1 | 10/2015 | Chin | |
| 2015/0305689 A1 | 10/2015 | Gourmelon et al. | |
| 2015/0313484 A1 | 11/2015 | Burg et al. | |
| 2015/0320328 A1 | 11/2015 | Albert | |
| 2015/0332012 A1 | 11/2015 | Edelson et al. | |
| 2015/0342538 A1 | 12/2015 | St. Pierre et al. | |
| 2015/0366469 A1 | 12/2015 | Harris et al. | |
| 2015/0366492 A1* | 12/2015 | De Haan | A61B 5/7214 |
| | | | 600/323 |
| 2015/0366518 A1 | 12/2015 | Sampson | |
| 2016/0000376 A1 | 1/2016 | Murray et al. | |
| 2016/0022220 A1 | 1/2016 | Lee et al. | |
| 2016/0089033 A1* | 3/2016 | Saponas | A61B 5/0205 |
| | | | 600/483 |
| 2016/0120434 A1 | 5/2016 | Park et al. | |
| 2016/0270668 A1 | 9/2016 | Gil | |
| 2016/0270677 A1* | 9/2016 | Lin | A61B 5/02427 |
| 2016/0360971 A1 | 12/2016 | Gross et al. | |
| 2016/0360986 A1 | 12/2016 | Lange | |
| 2016/0361003 A1 | 12/2016 | Lange et al. | |
| 2016/0361004 A1 | 12/2016 | Lange et al. | |
| 2017/0014037 A1 | 1/2017 | Coppola et al. | |
| 2017/0156593 A1 | 6/2017 | Ferber et al. | |
| 2017/0202459 A1 | 7/2017 | Cao | |
| 2017/0258406 A1 | 9/2017 | Lange | |
| 2018/0098705 A1* | 4/2018 | Chaturvedi | A61B 5/6884 |
| 2018/0132794 A1 | 5/2018 | Lange | |
| 2018/0247713 A1 | 8/2018 | Rothman | |
| 2019/0015014 A1 | 1/2019 | Lange | |
| 2021/0145310 A1 | 5/2021 | Lange | |

(56) References Cited

U.S. PATENT DOCUMENTS

FOREIGN PATENT DOCUMENTS

| | | |
|---|---|---|
| CN | 107920786 A | 4/2018 |
| EP | 2430975 A1 | 3/2012 |
| EP | 3307146 | 4/2018 |
| EP | 3307150 | 4/2018 |
| EP | 3307162 | 4/2018 |
| EP | 3493734 A1 | 6/2019 |
| EP | 3849407 A1 | 7/2021 |
| WO | WO0047108 A1 | 8/2000 |
| WO | WO2001015597 | 3/2001 |
| WO | WO2006048701 A2 | 5/2006 |
| WO | WO2014022906 A1 | 2/2014 |
| WO | WO2015047015 A1 | 4/2015 |
| WO | WO2015070030 A1 | 5/2015 |
| WO | WO2015197383 A1 | 12/2015 |
| WO | WO2016110804 A1 | 7/2016 |
| WO | WO2016199121 A1 | 12/2016 |
| WO | WO2016199122 A1 | 12/2016 |
| WO | WO2016199123 A1 | 12/2016 |
| WO | WO2016199124 A1 | 12/2016 |
| WO | WO2017141131 A1 | 8/2017 |
| WO | WO2017158585 A1 | 9/2017 |
| WO | WO2018025257 A1 | 2/2018 |
| WO | WO2018085563 A1 | 5/2018 |
| WO | WO2019130296 A1 | 7/2019 |
| WO | WO2020053858 A1 | 3/2020 |

OTHER PUBLICATIONS

Non-Final Office Action, dated Oct. 5, 2016, U.S. Appl. No. 14/738,666, filed Jun. 12, 2015.
Arza et al., "Pulse Transit Time and Pulse Width as Potential Measure for estimating Beat-to-Beat Systolic and Diastolic Blood Pressure", Computing in Cardiology 2013, pp. 887-890.
Ye et al., "Estimation of Systolic and Diastolic Pressure using the Pulse Transit Time", International Journal of Medical, Health, Biomedical, Bioengineering and Pharmaceutical Engineering vol. 4. No. 7, 2010, pp. 303-308.
International Search Report and Written Opinion dated Jul. 11, 2016 in Patent Cooperation Treaty Application No. PCT/IL2016/050511 filed May 15, 2016, pp. 1-19.
International Search Report and Written Opinion dated Aug. 18, 2016 in Patent Cooperation Treaty Application No. PCT/IL2016/050514 filed May 15, 2016, pp. 1-20.
International Search Report and Written Opinion dated Aug. 29, 2016 in Patent Cooperation Treaty Application No. PCT/IL2016/050513 filed May 15, 2016, pp. 1-18.
Patent Cooperation Treaty Application No. PCT/IL2016/050512, "International Search Report" and "Written Opinion of the International Searching Authority," dated Sep. 18, 2016, 9 pages.
"International Search Report" and "Written Opinion of the International Searching Authority," Patent Cooperation Treaty Application No. PCT/IL2017/050242, dated Jun. 13, 2017, 12 pages.
Abtahi, Farhad, "Feasibility of Fetal EEG Recording," Master's Thesis, Department of Signal and System, Chalmers University of Technology, Gothenburg, Sweden, Jan. 1, 2011, 51 pages.
Richardson, Kelly et al., "Electrocardiographic damage scores and cardiovascular mortality," American Heart Journal vol. 149, No. 3, Mar. 1, 2005, pp. 458-463.
Final Office Action, dated Mar. 22, 2017, U.S. Appl. No. 14/738,636, filed Jun. 12, 2015.
Final Office Action, dated Mar. 29, 2017, U.S. Appl. No. 14/738,666, filed Jun. 12, 2015.
Advisory Action, dated Jun. 16, 2017, U.S. Appl. No. 14/738,636, filed Jun. 12, 2015.
Advisory Action, dated Jun. 23, 2017, U.S. Appl. No. 14/738,666, filed Jun. 12, 2015.
"International Search Report" and "Written Opinion of the International Searching Authority," Patent Cooperation Treaty Application No. PCT/IL2017/050826, dated Oct. 23, 2017, 9 pages.
"Extended European Search Report," European Patent Application No. 16807014.2, dated Oct. 22, 2018, 8 pages.
"Extended European Search Report," European Patent Application No. 16807015.9, dated Jan. 21, 2019, 10 pages.
Gözde, Ateş et al., "Measuring of Oxygen Saturation Using Pulse Oximeter Based on Fuzzy Logic," Medical Measurements and Applications Proceedings (MEMEA), 2012 IEEE International Symposium, May 18, 2012, pp. 1-6.
"Extended European Search Report," European Patent Application No. 16807013.4, dated Jan. 17, 2019, 7 pages.
"Office Action," European Patent Application No. 16807013.4, dated Aug. 27, 2019, 6 pages.
"International Search Report" and "Written Opinion of the International Searching Authority," Patent Cooperation Treaty Application No. PCT/IL2019/051018, dated Dec. 17, 2019, 14 pages.
"International Search Report" and "Written Opinion of the International Searching Authority," Patent Cooperation Treaty Application No. PCT/IL2018/051384, dated Mar. 14, 2019, 15 pages.
"Notice of Allowance," European Patent Application No. 16807013. 4, dated May 26, 2020, 7 pages.
"Office Action," European Patent Application No. 16807015.9, dated Aug. 6, 2020, 7 pages.
"Extended European Search Report," European Patent Application No. 17836517.7, dated Feb. 25, 2020, 5 pages.
"Office Action," Chinese Patent Application No. 201680042023.6, dated Mar. 20, 2020, 10 pages.
"Notice of Allowance", European Patent Application No. 16807015. 9, dated Mar. 9, 2021, 7 pages.
"Office Action", European Patent Application No. 16807014.2, dated Apr. 30, 2021, 6 pages.
Sam et al., "Feasibility of single-arm single-lead ECG biometrics", 22nd European Signal Processing Conference (EUSIPCO), Sep. 1, 2014, pp. 2525-2529.
"Extended European Search Report", European Patent Application No. 18897389.5, dated Aug. 4, 2021, 9 pages.
Zhang et al., "Theoretical Study on the Effect of Sensor Contact Force on Pulse Transmit Time", IEEE Transactions on Biomedical Engineering, Sep. 2007, 10 pages.

\* cited by examiner

```
┌─────────────────────────────────────────────────────────────┐
│ Record, by a wearable device, substantially simultaneously an│
│   electrocardiogram (ECG) and photoplethysmogram (PPG),      │
│       wherein the PPG is measured at a blood artery          │
│                            602                                │
└─────────────────────────────────────────────────────────────┘
                              │
                              ▼
┌─────────────────────────────────────────────────────────────┐
│  Analyze, by at least one processor, the ECG and the PPG to │
│  determine a pulse transit time (PTT), a pulse rate (PR), and a│
│  diameter parameter, wherein the diameter parameter includes │
│    one of a diameter of the blood artery and a change in the │
│                   diameter of the blood artery               │
│                            604                                │
└─────────────────────────────────────────────────────────────┘
                              │
                              ▼
┌─────────────────────────────────────────────────────────────┐
│ Determine, by the at least one processor and using a pre-defined│
│ model, a blood pressure (BP) based on the PTT, the PR, and the │
│ diameter of parameter, wherein the pre-defined model establishes│
│ a relationship between the PTT, the PR, the diameter parameter,│
│                        and the BP                             │
│                            606                                │
└─────────────────────────────────────────────────────────────┘
```

FIG. 6

BLOOD PRESSURE MEASUREMENT USING A WEARABLE DEVICE

CROSS-REFERENCE TO RELATED APPLICATIONS

The present application is a Continuation in Part of U.S. patent application Ser. No. 14/738,666, titled "Monitoring Health Status of People Suffering from Chronic Diseases," filed on Jun. 12, 2015, and is a Continuation in Part of U.S. patent application Ser. No. 14/738,636, titled "Wearable Device Electrocardiogram," filed on Jun. 12, 2015, and is also a Continuation in Part of U.S. patent application Ser. No. 14/738,711, titled "Pulse Oximetry," filed on Jun. 12, 2015. The disclosures of the aforementioned applications are incorporated herein by reference for all purposes.

FIELD

The present application relates to systems and methods for monitoring the health status of people, and more specifically to systems and methods for continuous or intermittent measurement of non-invasive blood pressure (NIBP).

BACKGROUND

It should not be assumed that any of the approaches described in this section qualify as prior art merely by virtue of their inclusion in this section.

Blood pressure (BP) is one of the basic medical parameters used to diagnose human health condition. The most accurate methods for BP measurements involve insertion of a catheter into a human artery. However, the BP measurements using a catheter are invasive and costly since they require a medical professional to perform the measurements and, typically, can only be performed in a medical facility environment.

Less accurate methods for BP measurements include use of an inflatable cuff to pressurize a blood artery. There are numerous cuff-based portable devices for BP measurements that patients can use at home and do not require assistance of a medical professional. However, cuff-based measurements require inflation and deflation of the inflatable cuff. Therefore, such devices are cumbersome to use and not suitable for ongoing BP measurements.

Some cuff-less devices for BP measurements use an electrical sensor to measure an electrocardiogram (ECG) and optical sensors to measure a photoplethysmogram (PPG). The ECG and PPG can be analyzed to determine pulse transit time (PTT). Because the PTT is in-part inversely proportional to the BP, the BP can in some cases be determined from the PTT using a pre-defined relationship. However, changes in a cardio-vascular status of a patient require often re-calibration of PTT based blood pressure measurements. Cuff-less devices can potentially provide continuous monitoring of the BP while imposing a minimal burden on normal activities when worn on various body parts such as a finger, a wrist, or an ankle.

Determining the BP based on the PTT alone may not be sufficiently accurate because of other cardiovascular parameters affecting hemodynamics such as vascular resistance, cardiac output, pulse rate (PR), temperature of a finger (if PPG is measured at the finger), and so forth. To compensate for influences of other parameters, some existing techniques for measuring of BP using the PPG include applying correction factors to account for the vascular resistance and age of patient. The correction factors can be determined by an empirical formula. Some other techniques attempt to determine compensation factors to compensate for various additional influences (for example, contacting force to sensors, nervous activity and cardiac output of patient, and ambient temperature). The compensation factors can be determined using a calibration process.

However, all currently known methods for cuff-less, non-inflatable BP or NIBP monitoring require frequent re-calibration to compensate for unaccounted changes in cardiovascular status of a patient. Therefore, there is a clear need for an NIBP monitoring which can account for changes in the cardiovascular status and does not require a frequent re-calibration.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to one aspect of the present disclosure, systems and methods for blood pressure measurement are provided. An example method includes simultaneous recording, by a wearable device, of an ECG and a PPG. The PPG is measured at a blood artery. The method includes analyzing, by at least one processor, the ECG and the PPG to determine a PTT, a PR, and a diameter parameter. The diameter parameter includes one of the diameter of the blood artery or a change in the diameter of the blood artery. The method includes determining, by the at least one processor and using a pre-defined model, a BP based on the PTT, PR and diameter parameter. The pre-defined model establishes a relationship between at least the PTT, PR, diameter parameter, and BP.

In some embodiments, the pre-defined model includes regression analysis, wherein the PTT, PR, and diameter parameter are explanatory variables and the BP is a dependent variable.

In certain embodiments, the pre-defined model is trained using statistical data obtained during a calibration process, with the statistical data including the PTT, PR, and diameter parameter measured with the wearable device and corresponding values of the BP measured with an external device.

In some embodiments, the PTT is determined as a shift in time between a certain feature in the ECG and an associated feature in the PPG. The certain feature in the ECG and the associated feature in PPG correspond to the same heartbeat. The feature may include a certain peak or landmark in the ECG or PPG.

In some embodiments, the PTT is determined as a shift in time between a certain waveform of the ECG and an associated waveform in the PPG, with the certain ECG waveform and the associated second PPG waveform corresponding to the same heartbeat.

In some embodiments, the PR is determined as a time period between two peaks associated with two consecutive heart beats in the ECG.

In some embodiments, the PPG includes intensity of a light reflected from the blood artery. In certain embodiments, a wavelength of the light is isosbestic relative to light absorption by blood in the blood artery.

In some embodiments, the change in the diameter of the blood artery is determined using the following equation:

$$\left(\frac{AC}{DC}\right) = c*(\Delta\ d),$$

wherein DC is a direct current component of the PPG, the AC is an alternating current component of the PPG, c is an absorption coefficient of the blood in the blood artery, and Δd is the change of the diameter of the blood artery during a heartbeat cycle.

In some embodiments, the blood artery includes a radial artery at a wrist.

According to another example embodiment of the present disclosure, the steps of the method for blood pressure measurement are stored on a non-transitory machine-readable medium comprising instructions, which when implemented by one or more processors perform the recited steps.

Other example embodiments of the disclosure and aspects will become apparent from the following description taken in conjunction with the following drawings.

BRIEF DESCRIPTION OF THE DRAWINGS

Embodiments are illustrated by way of example and not limitation in the figures of the accompanying drawings, in which like references indicate similar elements.

FIG. 6 is a flow chart showing an example method for performing blood pressure measurement.

DETAILED DESCRIPTION

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical and electrical changes can be made without departing from the scope of what is claimed. The following detailed description is, therefore, not to be taken in a limiting sense, and the scope is defined by the appended claims and their equivalents.

The present disclosure provides systems and methods for performing blood pressure measurement. Embodiments of the present disclosure allow for continuous or intermittent measuring of blood pressure of a patient in a non-intrusive manner while, for example, the patient is at home, at work, outdoors, traveling, or is located at some other stationary or mobile environment. Embodiments of the present disclosure include a wearable device. The wearable device can be worn at a wrist, ankle, chest, neck, or positioned at other sites on a human body. The wearable device can allow measuring blood pressure of the patient without requiring the patient to take an active role in the process. The blood pressure data collected over an extended period of time can be analyzed to detect and track trends in medical parameters and to make conclusions concerning symptoms and a progression of one or more chronic diseases from which the patient may suffer.

According to some example embodiments, methods for performing blood pressure measurements include recording simultaneously, by a wearable device, an ECG and a PPG. The PPG is measured at a blood artery. The method further includes analyzing, by at least one processor, ECG and PPG to determine a PTT, a PR, and a diameter parameter. The diameter parameter includes one of the diameter of the blood artery or a change in the diameter of the blood artery. The method further includes determining, by the at least one processor and using a pre-defined model, including at least a BP based on PTT, PR and the diameter parameter. The pre-defined model establishes a relationship between the at least a PTT, PR, the diameter parameter, and BP.

Figure 1:
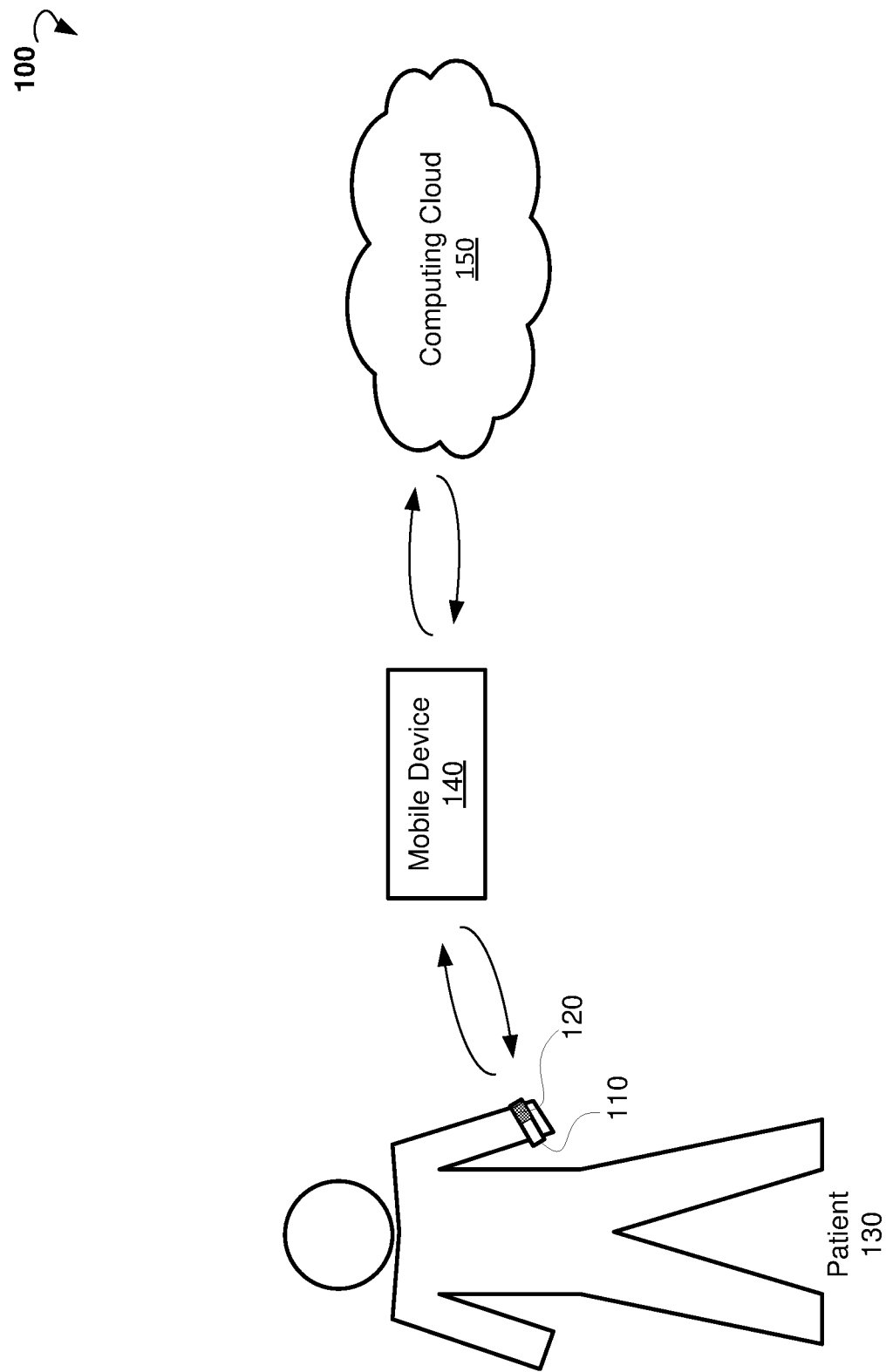
FIG. 1 is a block diagram showing an example system for performing a blood pressure measurement using a wearable device.

Referring now to FIG. 1, an example system 100 for performing blood pressure measurements is shown. The system 100 can include at least a wearable device 110. The wearable device 110 can include sensors 120. In some embodiments, the wearable device 110 is worn by a patient 130 (for example, on a wrist, ankle, earlobe, neck, chest, fingertip, and the like) for an extended period of time. In various embodiments, the wearable device 110 can be carried out as a watch, a bracelet, a wristband, a belt, a neck band, and the like.

The wearable device 110 can be operable to constantly collect, via sensors 120, sensor data from a patient 130. Based on the sensor data, the wearable device 110 can be operable to provide PPG and ECG. The PPG and ECG can be further used to obtain further medical parameters (for example, pulse rate, pulse transition time, blood pressure, and so forth).

In some embodiments, the system 100 includes a mobile device 140. The mobile device 140 can be communicatively coupled to the wearable device 110. In various embodiments, the mobile device 140 is operable to communicate with the wearable device 110 via a wireless connection such as, for example, Wi-Fi, Bluetooth, Infrared (IR), and the like. The mobile device 140 can include a mobile phone, a smart phone, a phablet, a tablet computer, a notebook, and so forth. The mobile device 140 can be operable to receive the sensor data and analyze the sensor data to provide ECG and PPG.

In further embodiments, the system 100 may include a cloud-based computing resource also referred to as a computing cloud 150. In some embodiments, the computing cloud 150 includes one or more server farms/clusters comprising a collection of computer servers and is co-located with network switches and/or routers. In certain embodiments, the mobile device 140 is communicatively coupled to the computing cloud 150. The mobile device 140 can be operable to send the sensor data to the computing cloud 150 for further analysis (for example, for extracting medical parameters from the ECG and PPG and storing the results). The computing cloud 150 can be operable to run one or more applications and to provide reports regarding a health status of the patient, based on trends in medical parameters over time.

Figure 2:
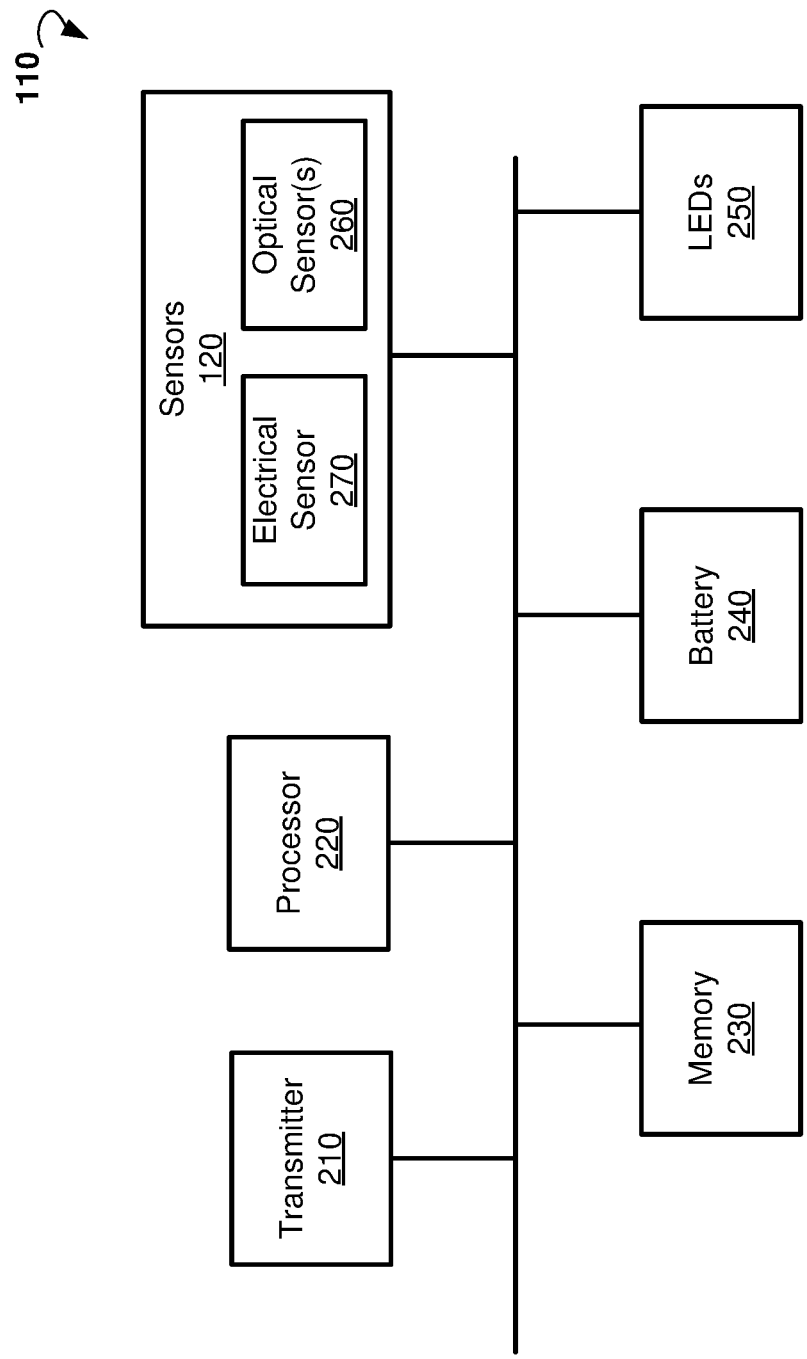
FIG. 2 is a block diagram showing components of an example device for performing blood pressure measurement.

FIG. 2 is a block diagram illustrating components of wearable device 110, according to an example embodiment.

The example wearable device 110 includes a transmitter 210, a processor 220, memory 230, a battery 240, light-emitting diodes (LEDs) 250, optical sensor(s) 260, and electrical sensor 270. The wearable device 110 may comprise additional or different components to provide a particular operation or functionality. Similarly, in other embodiments, the wearable device 110 includes fewer components that perform similar or equivalent functions to those depicted in FIG. 2.

The transmitter 210 can be configured to communicate with a network such as the Internet, a Wide Area Network (WAN), a Local Area Network (LAN), a cellular network, and so forth, to send data streams (for example sensor data, PPG data, and messages).

The processor 220 can include hardware and/or software, which is operable to execute computer programs stored in memory 230. The processor 220 can use floating point operations, complex operations, and other operations, including processing and analyzing data obtained from electrical sensor 270 and optical sensor(s) 260.

In some embodiments, the battery 240 is operable to provide electrical power for operation of other components of the wearable device 110. In some embodiments, the battery 240 is a rechargeable battery. In certain embodiments, the battery 240 is recharged using an inductive charging technology.

In various embodiments, the LEDs 250 are operable to emit light signals. The light signals can be of a red wavelength (typically 660 nm) or infrared wavelength (660 nm). Each of the LEDs 250 is activated separately and accompanied by a "dark" period where neither of the LEDs 250 is on to obtain ambient light levels. In some embodiments, a single LED 250 can be used to emit both the infrared and red light signals. The lights can be absorbed by human blood (mostly by hemoglobin). The oxygenated hemoglobin absorbs more infrared light while deoxygenated hemoglobin absorbs more red light. Oxygenated hemoglobin allows more red light to pass through while deoxygenated hemoglobin allows more infrared light to pass through. In some embodiments of the present disclosure, the LEDs 250 are also operable to emit light signals of isosbestic wavelengths (typically 810 nm and 520 nm). Both oxygenated hemoglobin and deoxygenated hemoglobin absorb the light of the isosbestic wavelengths equally.

The optical sensor(s) 260 (typically a photodiode) can receive light signals modulated by human tissue. Intensity of the modulated light signal represents a PPG. Based on the changes in the intensities of the modulated light signals, one or more medical parameters, such as, for example, oxygen saturation, arterial blood flow, pulse rate, and respiration, can be determined.

The LEDs 250 and optical sensor(s) 260 can be utilized in either a transmission or a reflectance mode for pulse oximetry. In the transmission mode, the LEDs 250 and optical sensor(s) 260 are typically attached or clipped to a translucent body part (e.g., a finger, toe, and earlobe). The LEDs 250 are located on one side of the body part while the optical sensor(s) 260 are located directly on the opposite site. The light passes through the entirety of the body part, from one side to the other, and is thus modulated by the pulsating arterial blood flow. In the reflectance mode, the LEDs 250 and optical sensor(s) 260 are located on the same side of the body part (e.g. a forehead, a finger, and a wrist), and the light is reflected from the skin and underlying near-surface tissues back to the optical sensor(s) 260.

Figure 3:
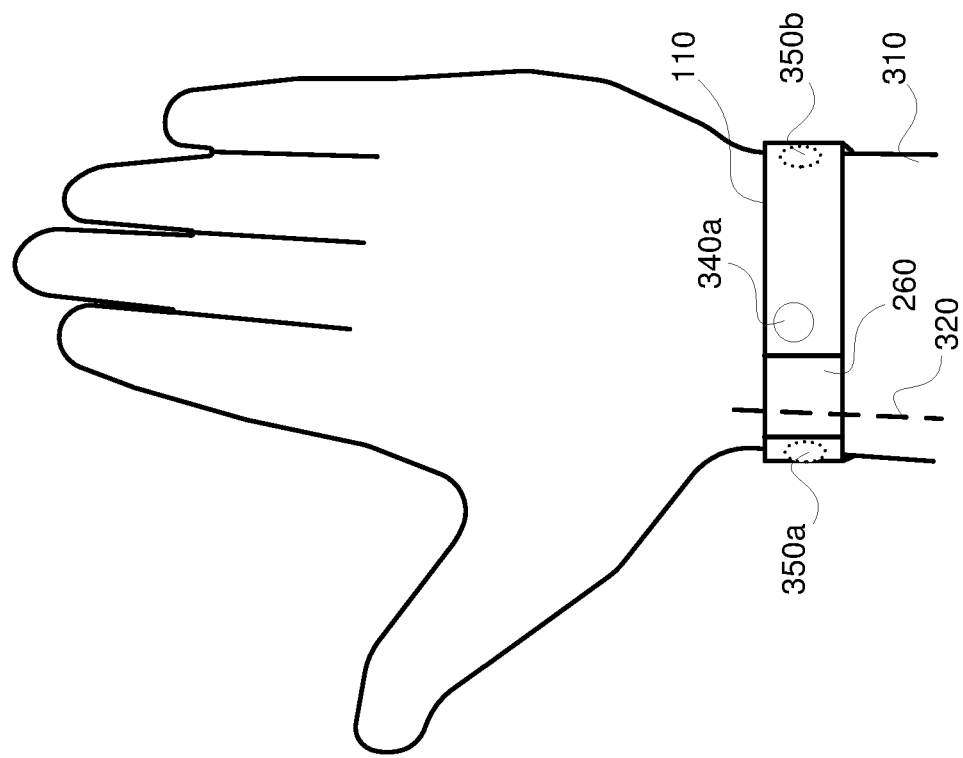
FIG. 3 is block diagram illustrating an example device for measuring arterial blood pressure from a wrist.

FIG. 3 is a block diagram illustrating an example wearable device 110 placed around a wrist of a patient. In the example of FIG. 3, the wearable device 110 is carried out in a shape of a watch, a ring, and/or a bracelet.

The electrical sensor 270 can include a differential amplifier operable to measure the electrical signal from the wrist. The electrical sensor 270 can include two active amplifier input plates embedded in the wearable device at opposite ends. In some embodiments, the first input plate (not shown) can be placed above the outer side of the wrist, and the second input plate 340a can be placed beneath the inner side of the wrist. Alternatively or additionally, in other embodiments, input plates 350a and 350b can be placed in contact with, respectively, the left and right sides of the wrist.

In some embodiments, the optical sensor(s) 260 can be placed beneath a pulsating artery travelling along the arm and into a wrist 310. In some embodiments, a radial artery 320 passing in the inner wrist is used for measurements by the optical sensor(s) 260. In other embodiments, other arteries such as the ulnar artery, may be used. An external light source generating constant lighting can be used to radiate the pulsating artery. A beam reflected from the pulsating artery can be intercepted by the optical sensor(s) 260. In certain embodiments, a light of isosbestic wavelength is used to radiate the pulsating artery.

Figure 4:
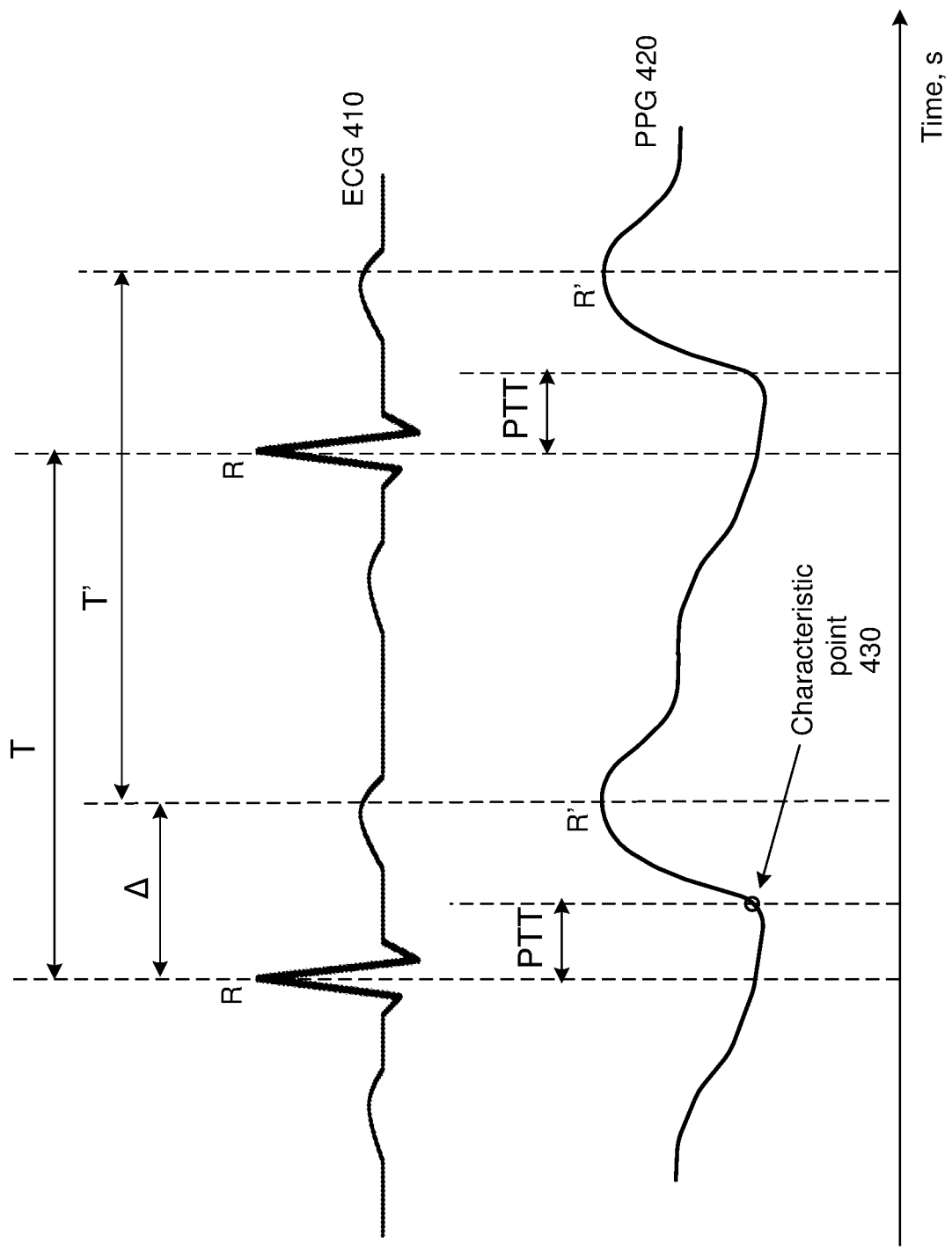
FIG. 4 shows an example plot of an ECG and an example plot of a PPG.

FIG. 4 shows plots of an example an example plot of an ECG 410, and an example plot of a PPG 420. The ECG 410 can be recorded with electrical sensor 270 using input plates placed on the wearable device 110. The ECG 410 can include R peaks corresponding to heart beats. Taking measurements from a single hand or a single wrist is challenging because the difference in voltages between measured locations is miniscule. The electrical signal measured at the wrist can include an ECG 410 and a noise. The noise can be caused by muscle activity, patient movements, and so forth. The noise component can be larger than the ECG. In some embodiments, the signal-to-noise ratio (SNR) is in the range of −40 dB to −60 dB. An example method for measuring a "clean" ECG from a wrist is described in U.S. Patent application Ser. No. 14/738,666, titled "Wearable Device Electrocardiogram," filed on Jun. 12, 2015.

The PPG 420 can be obtained by sensing a change in the color of skin. The change of the skin color is caused by a blood flow in a pulsating artery. In some embodiments, the PPG 420 can include peaks R' related to the heart beats. Since it takes a time for blood to flow from the heart to the wrist, the peaks R' are shifted by time periods A relative to the heart beats R in ECG 420. In some embodiments, shifts A can be measured as shift of a waveform of PPG (complex of PPG corresponding to period T' in FIG. 4) relative to a waveform of ECG (complex of ECG corresponding to period T in FIG. 4).

In various embodiments, ECG 410 and PPG 420 are used to estimate a PTT. In some embodiments, PTT is defined as a time interval between the R peak in ECG 410 and characteristic point 430 located at the bottom of the PPG 420. PTT is a parameter which inversely correlates to BP. PTT decreases as BP increases and PTT increases as BP decreases. Therefore, PTT can be used to estimate BP. In some embodiments, a regression equation can be derived to establish a relation between PTT and BP. The regression equation can be established for both systolic BP and diastolic BP. Alternatively in other embodiments, other mathematical models, such as neural networks, may be used to establish the relation between the PTT and BP.

The location of characteristic point 430 can be uncertain or hard to detect. For example, a shape of PPG at a foot can be diffused when a pulse rate is high. Therefore, in some embodiments, when location of characteristic point 430 is uncertain or hard to detect, shifts between specific features of the ECG and PPG (such as certain landmarks or peaks) corresponding to the same heartbeat are used as an estimate for PTT. In certain embodiments, PTT is estimated based on shifts between waveforms of ECG and PPG corresponding to the same heartbeat.

PTT depends on the shape and cross-section area of a blood vessel (for example, a pulsating artery at which measurement is performed) since speed of blood travelling through the blood vessel depends on the cross-section area of the blood vessel and blood pressure.

According to various embodiments of the present disclosure, ECG and PPG are used to estimate PTT, PR, and diameter of the blood vessel or a change in the diameter of the blood vessel. In some embodiments, PTT, PR, and the diameter of the blood vessel or the change in the diameter of the blood vessel are then used to estimate BP. In some embodiments, PTT is determined based on ECG and PPG. PR can be found using a time period between two consecutive peaks in ECG or two consecutive peaks in PPG. In some embodiments, the diameter of the blood vessel or the change in the diameter of the blood vessel can be estimated using PPG.

Figure 5:
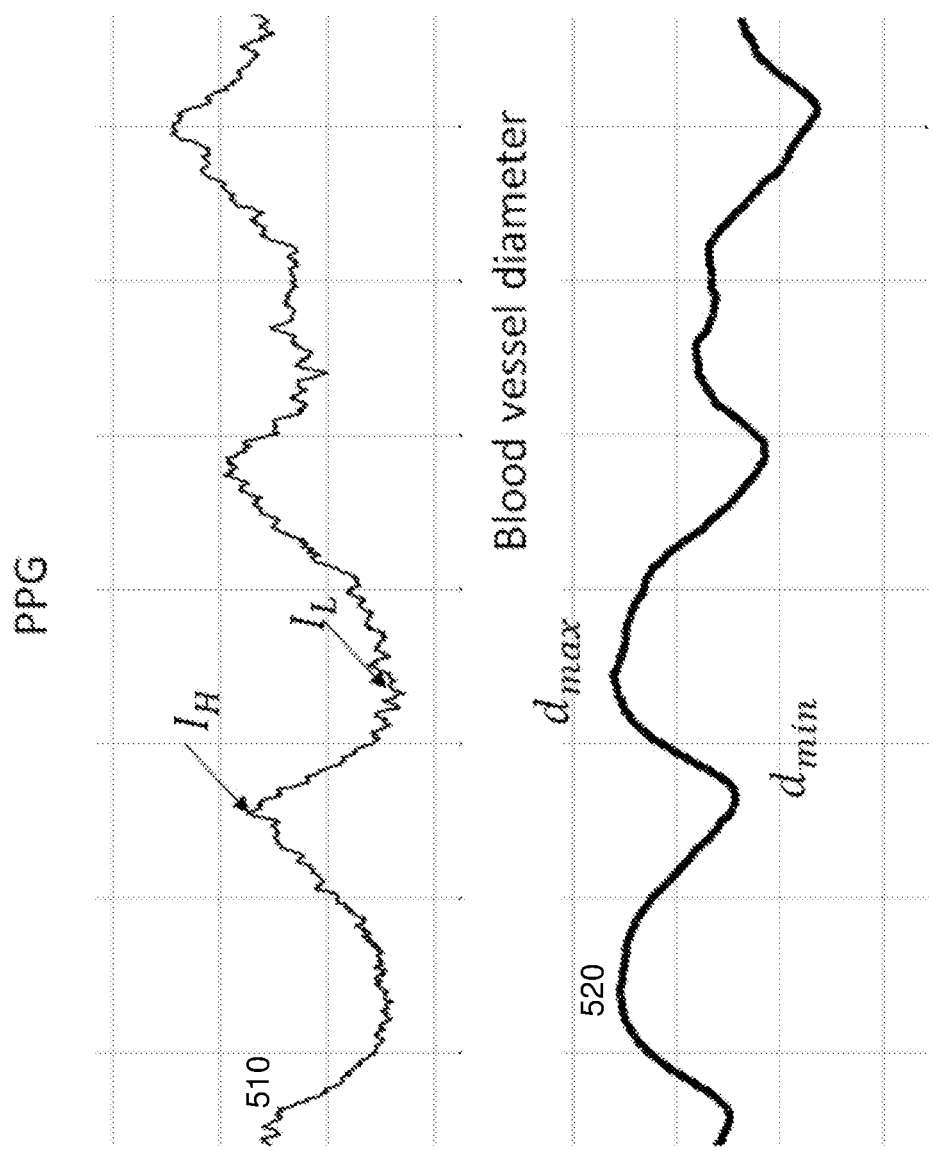
FIG. 5 shows an example plot of a PPG and an example plot of a blood vessel diameter.

FIG. 5 shows an example plot of PPG 510 and an example plot of blood vessel diameter 520. The PPG 510 represents the intensity I of the light signal as modulated by a human tissue mostly due to a blood flow in the blood vessel. The high peaks (maximums) $I_H$ of PPG 510 correspond to the low peaks dm of the blood vessel diameter 520, and the low peaks $I_L$ of the PPG 510 correspond to the high peaks $d_{max}$ of the blood vessel diameter 520.

In some embodiments, the detected PPG signal I, which is the intensity of light signal reflected from pulsating tissue, is modeled as follows:

$$I(t)=I_0*F*e^{-c*d(t)} \quad (1).$$

In formula (1), $I_0$ represents an incident light intensity, F indicates the absorption by pulsatile tissue, d(t) represents (arterial) blood vessel diameter, and c is overall absorption coefficient of blood hemoglobin derived from a mixture of both oxygen-saturated and non-oxygen saturated hemoglobin. Each of oxygen-saturated and non-oxygen saturated hemoglobin has its own particular value of absorption coefficient c for a particular wavelength of emitted light. Therefore, according to some embodiments, a light of isosbestic wavelength is used to radiate the pulsatile tissue allowing absorption coefficient c to remain constant and independent of SpO2 oxygen saturation. The light absorption at the isosbestic wavelength is independent of SpO2 oxygen saturation because when a light of an isosbestic wavelength is used, the reflection from the oxygenized blood is the same as reflection from the non-oxygenized blood. In some embodiments, the isosbestic wavelength includes a near infrared wavelength 810 nm (NIR) and a green wavelength 520 nm (green). The NIR wavelength is more suitable for deeper vessels as it has deeper penetration while the green wavelength is more suitable for shallow vessels.

As shown in FIG. 5, the blood vessel diameter 520 changes periodically with the rhythm of the heart rate. The low peaks of the blood vessel diameter $d_{min}$ correspond to the minimums of the absorption of the light by the blood and the high peaks of the light intensity $I_H$. The high peaks of the blood vessel diameter $d_{max}$ correspond to maximum absorption of the light by blood and the lowest peaks of the light intensity $I_L$. In some embodiments, the low peaks of the blood vessel diameter $d_{min}$ can be considered to be constant as they reflect lowest diastole. The high peaks of the blood vessel diameter $d_{max}$ may vary relatively slowly due to, for example, fluctuations of blood pressure.

In some embodiments, it can be assumed that $$I(t) \approx I_0*F*(1-c*d(t)) \quad (2).$$

Denoting further direct current (DC) component of PPG $$DC=I_0*F \quad (3)$$

and alternating current (AC) component $$AC=I_0*F*c*d(t) \quad (4),$$

an equation for determining blood vessel diameter d(t) can be written as:

$$\left(\frac{AC}{DC}\right) = c*d(t). \quad (5)$$

In equation (5), the AC component and DC component are found from PPG and absorption coefficient c is known. In some embodiments, change $d(t)_{max} - d(t)_{min}$ is used to estimate BP.

In other embodiments, BP is calculated from measured PTT, PR, and the diameter of the blood vessel or a change thereof using a pre-defined model. The pre-defined model describes a relationship between PTT, PR, and the diameter of the blood vessel and BP. In some embodiments, the pre-defined model is determined using statistical data collected during a calibration process. During the calibration process, a patient can wear the wearable device 110 to measure PTT, PR, and the diameter of the blood vessel or a change in the diameter of the blood vessel. Simultaneously, BP can be measured using an external device (for example, a conventional device for BP measurement). The calibration can be performed once at first usage of the wearable device 110 by a particular patient, and requires at least a single simultaneous measurement by the wearable device 110 and the external device. In other embodiments, several simultaneous measurements should be made to calibrate the wearable device 110 in a range of blood pressure values. The range of blood pressure values can be achieved by taking measurements at either or all the following: different times (hours of a day), different physical states of a patient, and different emotional states of the patient. Alternatively, lowering or elevating the arm and taking local blood pressure at the wrist with both an external device and the wearable device 110 can provide an effective means for mapping the PTT, PR, and diameter of the blood vessel or a change in the diameter of the blood vessel to a wide range of blood pressure values.

In some embodiments, the pre-defined model includes a three-dimensional model, wherein PTT, PR and the diameter of the blood vessel or a change in the diameter of the blood vessel are explanatory variables and systolic blood pressure is a dependent variable. Similarly, another three-dimensional model can be used to establish mathematical relationships between PTT, PR and diameter of blood vessel or a change in the diameter of the blood vessel as explanatory variables and diastolic blood pressure as a dependent variable.

FIG. 6 is a flow chart showing steps of a method 600 for performing BP measurement, according to some embodiments. The method 600 can be implemented using wearable device 110 described in FIGS. 2 and 3 and system 100 described in FIG. 1. The method 600 may commence in block 602 with substantially simultaneous recording, by a wearable device, an ECG and a PPG. In some embodiments, PPG is measured at a blood artery. In some embodiments, ECG and PPG are recorded at a wrist.

In block 604, the method 600 proceeds with analyzing ECG and PPG to determine a PTT, a PR, and a diameter parameter. The diameter parameter may include a diameter of the blood artery or a change in the diameter of the blood artery. In block 606, the method 600 determines, based on PTT, PR, and the diameter parameter, BP using a pre-defined model. The pre-defined model establishes a relationship between the PTT, the PR, the diameter parameter, and the BP. In some embodiments, analysis of ECG and PPG and determination of PTT, the PR, the diameter parameter, and BP is performed locally using processor of the wearable device. In other embodiments, analysis of ECG and PPG and determination of PTT, the PR, the diameter parameter, and BP can be carried out remotely by a mobile device connected to the wearable device or in a computing cloud.

Figure 7:
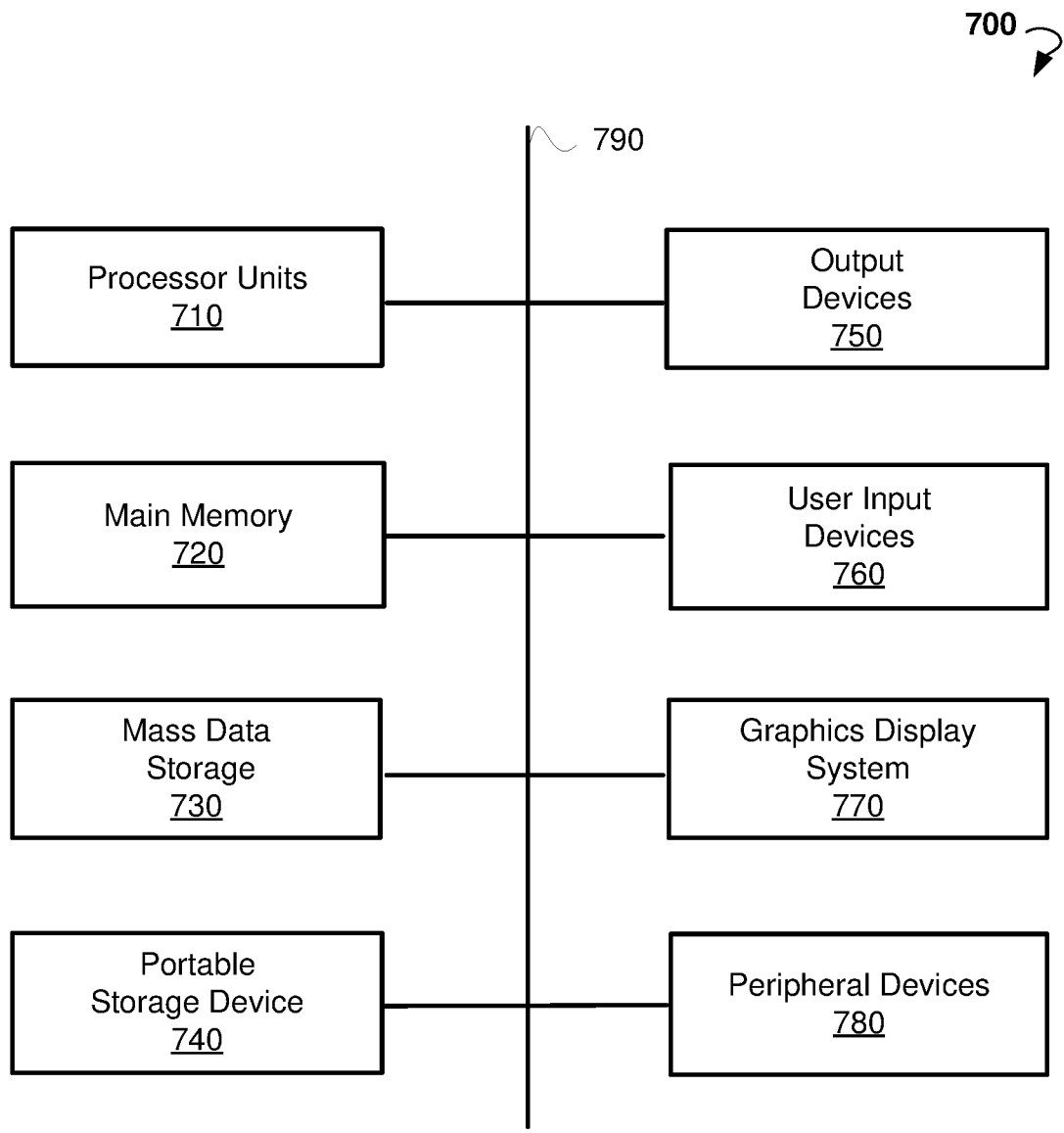
FIG. 7 shows a diagrammatic representation of a computing device for a machine, within which a set of instructions for causing the machine to perform any one or more of the methodologies discussed herein can be executed.

FIG. 7 illustrates a computer system 700 that may be used to implement embodiments of the present disclosure, according to an example embodiment. The computer system 700 may serve as a computing device for a machine, within which a set of instructions for causing the machine to perform any one or more of the methodologies discussed herein can be executed. The computer system 700 can be implemented in the contexts of the likes of computing systems, networks, servers, or combinations thereof. The computer system 700 includes one or more processor units 710 and main memory 720. Main memory 720 stores, in part, instructions and data for execution by processor units 710. Main memory 720 stores the executable code when in operation. The computer system 700 further includes a mass data storage 730, a portable storage device 740, output devices 750, user input devices 760, a graphics display system 770, and peripheral devices 780. The methods may be implemented in software that is cloud-based.

The components shown in FIG. 7 are depicted as being connected via a single bus 790. The components may be connected through one or more data transport means. Processor units 710 and main memory 720 are connected via a local microprocessor bus, and mass data storage 730, peripheral devices 780, the portable storage device 740, and graphics display system 770 are connected via one or more I/O buses.

Mass data storage 730, which can be implemented with a magnetic disk drive, solid state drive, or an optical disk drive, is a non-volatile storage device for storing data and instructions for use by processor units 710. Mass data storage 730 stores the system software for implementing embodiments of the present disclosure for purposes of loading that software into main memory 720.

The portable storage device 740 operates in conjunction with a portable non-volatile storage medium, such as a floppy disk, compact disk (CD), Digital Versatile Disc (DVD), or USB storage device, to input and output data and code to and from the computer system 700. The system software for implementing embodiments of the present disclosure is stored on such a portable medium and input to the computer system 700 via the portable storage device 740.

User input devices 760 provide a portion of a user interface. User input devices 760 include one or more microphones, an alphanumeric keypad, such as a keyboard, for inputting alphanumeric and other information, or a pointing device, such as a mouse, a trackball, stylus, or cursor direction keys. User input devices 760 can also include a touchscreen. Additionally, the computer system 700 includes output devices 750. Suitable output devices include speakers, printers, network interfaces, and monitors.

Graphics display system 770 includes a liquid crystal display or other suitable display device. Graphics display system 770 receives textual and graphical information and processes the information for output to the display device. Peripheral devices 780 may include any type of computer support device to add additional functionality to the computer system.

The components provided in the computer system 700 of FIG. 7 are those typically found in computer systems that may be suitable for use with embodiments of the present disclosure and are intended to represent a broad category of such computer components that are well known in the art. Thus, the computer system 700 can be a personal computer, handheld computing system, telephone, mobile computing system, workstation, tablet, phablet, mobile phone, server, minicomputer, mainframe computer, or any other computing system. The computer may also include different bus configurations, networked platforms, multi-processor platforms, and the like. Various operating systems may be used including UNIX, LINUX, WINDOWS, MAC OS, PALM OS, ANDROID, IOS, QNX, TIZEN and other suitable operating systems.

It is noteworthy that any hardware platform suitable for performing the processing described herein is suitable for use with the embodiments provided herein. Computer-readable storage media refer to any medium or media that participate in providing instructions to a central processing unit, a processor, a microcontroller, or the like. Such media may take forms including, but not limited to, non-volatile and volatile media such as optical or magnetic disks and dynamic memory, respectively. Common forms of computer-readable storage media include a floppy disk, a flexible disk, a hard disk, magnetic tape, any other magnetic storage medium, a CD Read Only Memory disk, DVD, Blu-ray disc, any other optical storage medium, RAM, Programmable Read-Only Memory, Erasable Programmable Read-Only Memory, Electronically Erasable Programmable Read-Only Memory, flash memory, and/or any other memory chip, module, or cartridge.

In some embodiments, the computer system 700 may be implemented as a cloud-based computing environment, such as a virtual machine operating within a computing cloud. In other embodiments, the computer system 700 may itself include a cloud-based computing environment, where the functionalities of the computer system 700 are executed in a distributed fashion. Thus, the computer system 700, when configured as a computing cloud, may include pluralities of computing devices in various forms, as will be described in greater detail below.

In general, a cloud-based computing environment is a resource that typically combines the computational power of a large grouping of processors (such as within web servers) and/or that combines the storage capacity of a large grouping of computer memories or storage devices. Systems that provide cloud-based resources may be utilized exclusively by their owners or such systems may be accessible to outside users who deploy applications within the computing infrastructure to obtain the benefit of large computational or storage resources.

The cloud may be formed, for example, by a network of web servers that comprise a plurality of computing devices, such as the computer system 700, with each server (or at least a plurality thereof) providing processor and/or storage resources. These servers may manage workloads provided by multiple users (e.g., cloud resource customers or other users). Typically, each user places workload demands upon the cloud that vary in real-time, sometimes dramatically. The nature and extent of these variations typically depends on the type of business associated with the user.

Thus, methods and systems for performing pulse oximetry have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A method for performing a blood pressure (BP) measurement, the method comprising:
    recording substantially simultaneously, by a wearable device, an electrocardiogram (ECG) and photoplethysmogram (PPG),
        wherein the PPG is measured at a blood artery of a limb, the PPG measurement including at least:
        emitting a light signal for a period of time; and
        detecting a modulated light signal, the modulated light signal originating from an interaction of the light signal with a human tissue, the human tissue including the blood artery and a non-pulsatile tissue;
    analyzing, by at least one processor, the ECG and the PPG measured at the blood artery to determine a pulse transit time (PTT) and a pulse rate (PR);
    determining, by the at least one processor and based on the PPG measured at the blood artery, a diameter parameter, wherein the diameter parameter includes one of a diameter of the blood artery and a change in the diameter of the blood artery, and the determining includes at least modifying the PPG by removing, from the PPG measured at the blood artery, an additive contribution resulting from a reflection of the light signal from a surface of a skin covering the blood artery and near-surface tissues underlying the skin and covering the blood artery and keeping, in the PPG measured at the blood artery, a contribution resulting from the reflection of the light signal from the blood artery unchanged, the additive contribution being predetermined using a calibration process, wherein the change in the diameter of the blood artery is determined based on a ratio $$\frac{AC}{DC},$$

wherein AC is an alternating current component of the modified PPG, and DC is a direct current component of the modified PPG; and
    determining, by the at least one processor and using a pre-defined model, a BP based on the PTT, the PR, and the diameter parameter, wherein the pre-defined model establishes a relationship between the PTT, the PR, the diameter parameter, and the BP.

2. The method of claim 1, wherein the pre-defined model includes a regression analysis, wherein the PTT, the PR, and the diameter parameter are explanatory variables and the BP is a dependent variable.

3. The method of claim 1, wherein the pre-defined model is trained using statistical data obtained in a calibration process, the statistical data including the PTT, the PR, and the diameter parameter measured with the wearable device and corresponding values of the BP measured with an external device.

4. The method of claim 1, wherein the PTT is determined as a shift in time between a certain feature in the ECG and an associated feature in the PPG, the certain feature and the associated feature corresponding to a same heartbeat.

5. The method of claim 1, wherein the PTT is determined as a shift in time between a first waveform of the ECG and a second waveform in the PPG, the first waveform and the second waveform corresponding to a same heartbeat.

6. The method of claim 1, wherein the PR is determined as a time period between two consecutive peaks in the ECG.

7. The method of claim 1, wherein the PPG includes an intensity of the light signal reflected from the blood artery.

8. The method of claim 7, wherein a wavelength of the light signal is isosbestic relative to a light absorption by blood in the blood artery.

9. The method of claim 1, wherein the change in the $$\left(\frac{AC}{DC}\right) = c * \Delta\ d,$$

diameter of the blood artery is determined using equation wherein DC is the direct current component of the modified PPG, AC is the alternating current component of the modified PPG, c is an absorption coefficient of blood in the blood artery, and $\Delta$ d is the change of the diameter of the blood artery.

10. The method of claim 1, wherein the blood artery is a radial artery of the limb.

11. A system for performing a blood pressure (BP) measurement, the system comprising:
    a wearable device operable to record simultaneously an electrocardiogram (ECG) and photoplethysmogram (PPG),
        wherein the PPG is measured at a blood artery of a limb, the PPG measurement including at least:
        emitting a light signal for a period of time;
        detecting a modulated light signal, the modulated light signal originating from an interaction of the light signal with a human tissue, the human tissue including the blood artery and a non-pulsatile tissue; and
    at least one processor communicatively coupled to the wearable device and operable to:
        analyze the ECG and the PPG measured at the blood artery to determine a pulse transit time (PTT) and a pulse rate (PR); and
        determine, based on the PPG measured at the blood artery, a diameter parameter, the diameter parameter including one of a diameter of the blood artery and a change in the diameter of the blood artery, wherein the determining includes at least modifying the PPG by removing, from the PPG measured at the blood artery, an additive contribution resulting from a reflection of the light signal from a surface of a skin covering the blood artery and near-surface tissues underlying the skin and covering the blood artery and keeping, in the PPG measured at the blood artery, a contribution resulting from the reflection of the light signal from the blood artery unchanged, the additive contribution being predetermined using a calibration process, wherein the change in the diameter of the blood artery is determined based on a ratio $$\frac{AC}{DC},$$

wherein AC is an alternating current component of the modified PPG, and DC is a direct current component of the modified PPG; and determine, based on the PTT, the PR, and the diameter parameter, a blood pressure (BP) using a pre-defined model, wherein the pre-defined model establishes a relationship between the PTT, the PR, the diameter parameter, and the BP.

12. The system of claim 11, wherein the pre-defined model includes a regression equation, wherein the PTT, the PR, and the diameter parameter are explanatory variables and the BP is a dependent variable.

13. The system of claim 11, wherein the pre-defined model is trained using statistical data obtained in a calibration process, the statistical data including the PTT, the PR, and the diameter parameter measured with the wearable device and corresponding values of the BP measured with an external device.

14. The system of claim 11, wherein the PTT is determined as a shift in time between a certain feature in the ECG and an associated feature in the PPG, the certain feature and the associated feature corresponding to a same heartbeat.

15. The system of claim 11, wherein the PTT is determined as a shift in time between a first waveform of the ECG and a second waveform in the PPG, the first waveform and the second waveform corresponding to a same heartbeat.

16. The system of claim 11, wherein the PR is determined as a time period between two consecutive peaks in the ECG.

17. The system of claim 11, wherein the PPG includes intensity of the light signal reflected from the blood artery.

18. The system of claim 17, wherein a wavelength of the light signal is isosbestic relative to light absorption by blood in the blood artery.

19. The system of claim 11, wherein the change in the diameter of the blood artery is determined using equation $$\left(\frac{AC}{DC}\right) = c * \Delta d,$$

wherein DC is the direct current component of the modified PPG, AC is the alternating current component of the modified PPG, c is an absorption coefficient of blood in the blood artery, and $\Delta d$ is the change of the diameter of the blood artery.

20. A non-transitory computer-readable storage medium having embodied thereon instructions, which when executed by at least one processor, perform steps of a method, the method comprising:

recording, by a wearable device, simultaneously an electrocardiogram (ECG) and photoplethysmogram (PPG), wherein the PPG is measured at a blood artery of a limb, the PPG measurement including at least:
emitting a light signal for a period of time; and
detecting a modulated light signal, the modulated light signal originating from an interaction of the light signal with a human tissue, the human tissue including the blood artery and a non-pulsatile tissue;

analyzing, by at least one processor, the ECG and the PPG measured at the blood artery to determine a pulse transit time (PTT) and a pulse rate (PR);

determining, by the at least one processor and based on the PPG measured at the blood artery, a diameter parameter, wherein the diameter parameter includes one of the blood artery and a change in a diameter of the blood artery and the determining includes at least modifying the PPG by removing, from the PPG measured at the blood artery, an additive contribution resulting from a reflection of the light signal from a surface of a skin covering the blood artery and near-surface tissues underlying the skin and covering the blood artery and keeping, in the PPG measured at the blood artery, a contribution resulting from the reflection of the light signal from the blood artery unchanged, the additive contribution being predetermined using a calibration process, wherein the change in the diameter of the blood artery is determined based on a ratio $$\frac{AC}{DC},$$

wherein AC is an alternating current component of the modified PPG, and DC is a direct current component of the modified PPG; and determining, by the at least one processor and using a pre-defined model, a blood pressure (BP) based on the PTT, the PR, and the diameter parameter, wherein the pre-defined model establishes a relationship between the PTT, the PR, the diameter parameter, and the BP.

* * * * *

UNITED STATES PATENT AND TRADEMARK OFFICE
CERTIFICATE OF CORRECTION

PATENT NO. : 11,160,461 B2
APPLICATION NO. : 15/226881
DATED : November 2, 2021
INVENTOR(S) : Daniel H. Lange Page 1 of 1

It is certified that error appears in the above-identified patent and that said Letters Patent is hereby corrected as shown below:

In the Claims

Column 12 Line 41, that portion reading:
"emitting a light signal for a period of time;"
Should read:
"emitting a light signal for a period of time; and"

Column 12 Line 51, that portion reading:
"pulse rate (PR); and"
Should read:
"pulse rate (PR);"

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*